(12) United States Patent
Hebrard

(10) Patent No.: US 10,041,529 B2
(45) Date of Patent: Aug. 7, 2018

(54) DEVICE FOR MEASURING THE WEAR OF A BALL-AND-SOCKET JOINT, BALL-AND-SOCKET JOINT INCORPORATING SAID DEVICE AND METHOD FOR MEASURING THE WEAR OF SUCH A BALL-AND-SOCKET JOINT

(71) Applicant: Yoann Hebrard, Sarras (FR)

(72) Inventor: Yoann Hebrard, Sarras (FR)

(73) Assignee: SKF AEROSPACE FRANCE S.A.S., Montigny-le-Bretonneux (FR)

( * ) Notice: Subject to any disclaimer, the term of this patent is extended or adjusted under 35 U.S.C. 154(b) by 300 days.

(21) Appl. No.: 14/572,842

(22) Filed: Dec. 17, 2014

(65) Prior Publication Data

US 2015/0176638 A1 Jun. 25, 2015

(30) Foreign Application Priority Data

Dec. 20, 2013 (FR) ...................................... 1363296

(51) Int. Cl.
*F16C 11/06* (2006.01)
*G01N 27/24* (2006.01)
(Continued)

(52) U.S. Cl.
CPC ........ *F16C 11/0647* (2013.01); *F16C 17/246* (2013.01); *G01B 7/144* (2013.01);
(Continued)

(58) Field of Classification Search
CPC ............... G06G 17/019; F16C 11/0623; F16C 11/0628; F16C 11/0633; F16C 11/0647;
(Continued)

(56) References Cited

U.S. PATENT DOCUMENTS 5,642,944 A * 7/1997 Dublin, Jr. .............. B61F 15/12
384/102
6,295,863 B1 * 10/2001 Ginder .................... G01M 3/04
403/27
(Continued)

FOREIGN PATENT DOCUMENTS

DE 19546084 C1 5/1997
EP 0060588 A1 9/1982
(Continued)

*Primary Examiner* — Tung X Nguyen
*Assistant Examiner* — Lee Rodak
(74) *Attorney, Agent, or Firm* — Bryan Peckjian; SKF USA Inc. Patent Dept.

(57) ABSTRACT

A device adapted to measure the wear of a ball-and-socket joint. The ball-and-socket joint comprising a first ring, which delimits a spherical housing, a second spherical ring, which is positioned concentrically in the housing of the first ring, and a lining, which is made from an elastically insulating material and is inserted between the second ring and the spherical housing of the first ring. A wear measuring feature includes at least two electrodes provided to be connected to the first ring and the second ring, respectively, or to the lining, so as to form a capacitor structure and a capacitance measuring device for measuring the capacity of the capacitor thus formed. The device further comprises an electronic circuit, which is a resonant circuit including the capacitor, an inductance and a resistance positioned in series.

9 Claims, 2 Drawing Sheets

(51) Int. Cl.
*F16C 17/24* (2006.01)
*G01B 7/14* (2006.01)
*G01D 5/24* (2006.01)

(52) U.S. Cl.
CPC ............... *G01N 27/24* (2013.01); *G01D 5/24* (2013.01); *Y10T 403/32631* (2015.01)

(58) Field of Classification Search
CPC ........ F16C 11/06; F16C 17/24; F16C 17/246; F16C 41/008; F16C 17/02; F16C 11/0614; F16C 11/0604; F16C 11/0652; F16C 11/0666; F16C 11/086; F16C 23/043; F16C 41/00; F16C 2326/05; F16C 2326/43; F16C 19/52; F16C 19/06; F16C 19/183; F16C 19/522; F16C 19/525; F16C 19/527; F16C 2233/00; F16C 2202/04; F16C 2204/72; F16C 23/045; F16C 23/086; G01L 5/0009; G01L 5/0014; G01L 5/162; G01L 5/223; Y10T 403/32704; Y10T 403/32631; B60G 2204/11; B60G 2204/416; B60G 2400/50; B60G 2204/60; B60G 2204/64; B60G 2401/10; B60G 2401/12; B60G 2401/25; B60G 2401/26; B60G 2400/60; B60G 2400/64; G01M 13/04; G01M 3/16; G01M 13/16; G01N 3/56; G01N 27/22; G01N 27/221; G01N 27/02; G01N 27/205; G01B 7/144; G01B 11/06; G01D 5/24; A61F 2/30; A61F 2/38; A61F 2/4657; A61F 2/28; A61F 2/32; A61F 2/36; A61F 2/3804; A61F 2/40; A61F 2002/4666; A61F 2002/488; A61B 5/4528; A61B 5/4851; A61B 5/0031; A61B 5/11
USPC ................................... 324/658–580
See application file for complete search history.

(56) References Cited

U.S. PATENT DOCUMENTS

| | | | |
|---|---|---|---|
| 7,001,785 B1* | 2/2006 | Chen ................. | G01R 27/2658 438/10 |
| 2006/0232408 A1* | 10/2006 | Nycz ..................... | G06F 19/323 340/572.1 |
| 2007/0089513 A1* | 4/2007 | Rosenau ................ | G01D 5/24 73/514.32 |
| 2007/0126587 A1* | 6/2007 | Nakajima ............. | F16C 41/008 340/572.8 |
| 2009/0087253 A1* | 4/2009 | Spratte ................ | B60G 17/019 403/131 |
| 2014/0103942 A1* | 4/2014 | Izrailit ................ | G01N 27/221 324/662 |
| 2014/0326079 A1* | 11/2014 | Maeda .................... | G01L 1/146 73/862.626 |
| 2015/0049970 A1* | 2/2015 | Carnahan ............. | F16C 17/246 384/448 |

FOREIGN PATENT DOCUMENTS

| | | |
|---|---|---|
| EP | 1602842 A1 | 12/2005 |
| FR | 2617923 A1 | 1/1989 |
| GB | 2430752 A | 4/2007 |
| JP | H0980096 A | 3/1997 |
| WO | 2012/149958 A1 | 11/2012 |

* cited by examiner

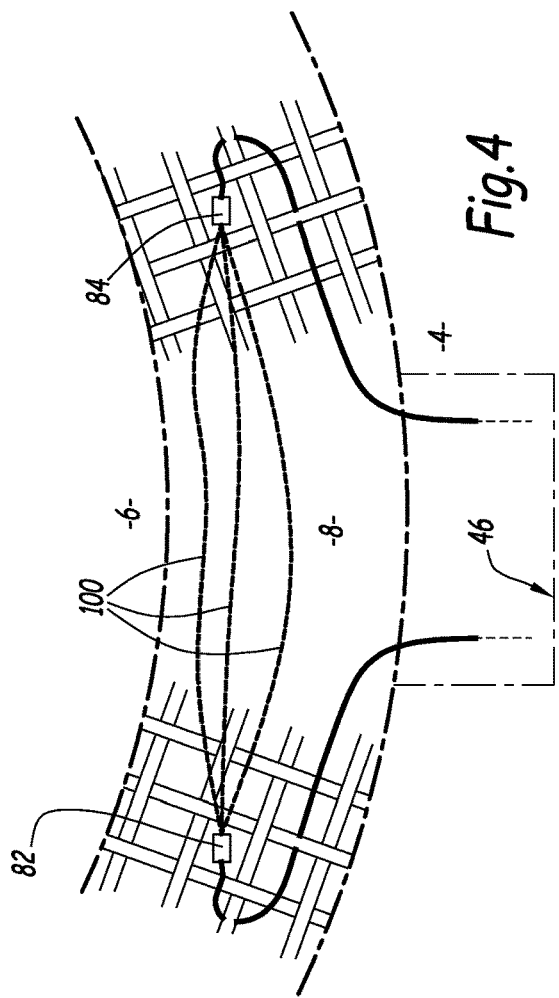
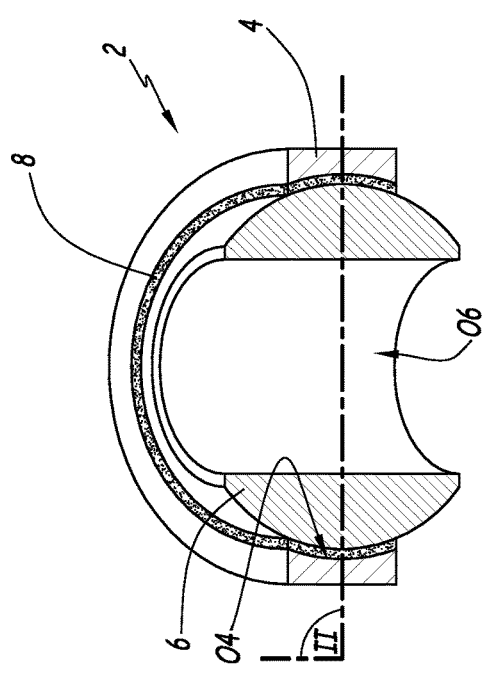

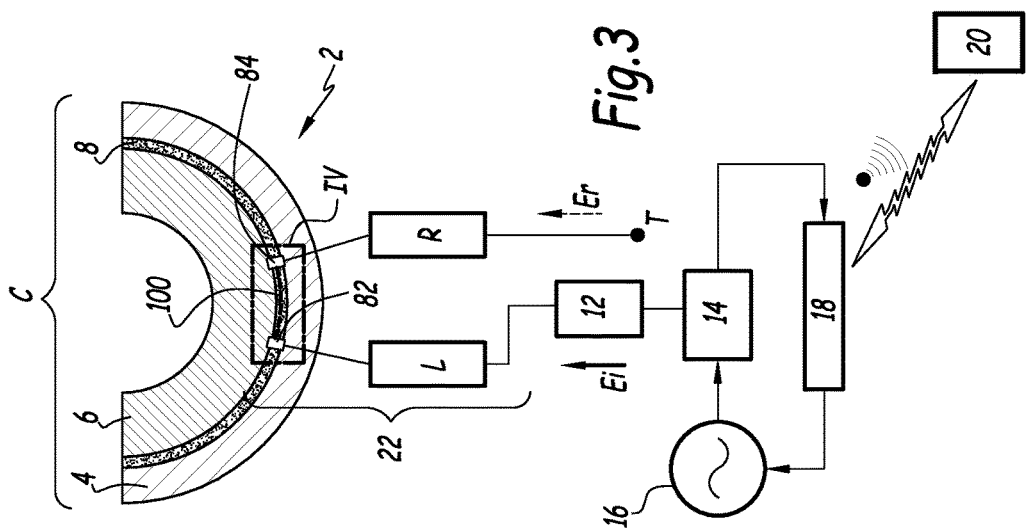
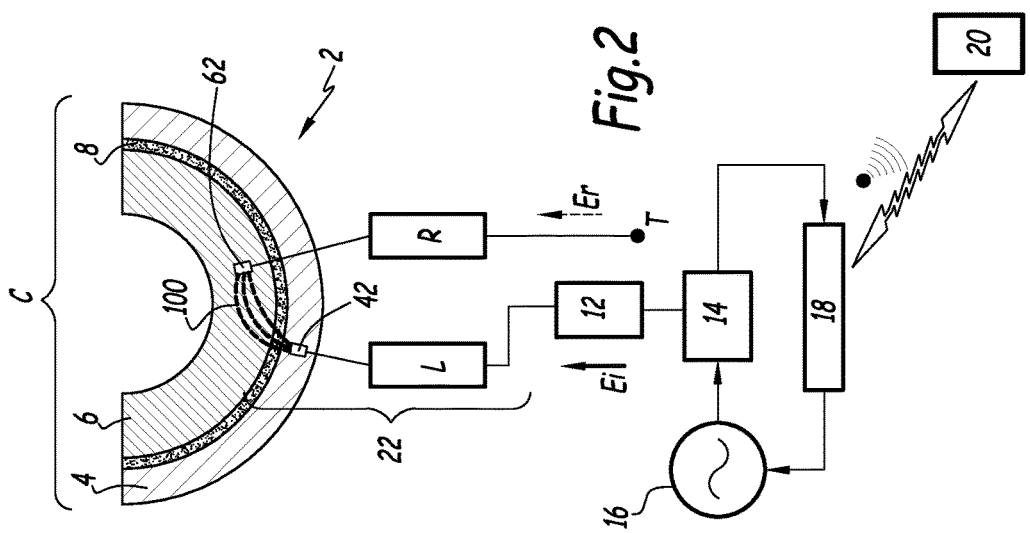

DEVICE FOR MEASURING THE WEAR OF A BALL-AND-SOCKET JOINT, BALL-AND-SOCKET JOINT INCORPORATING SAID DEVICE AND METHOD FOR MEASURING THE WEAR OF SUCH A BALL-AND-SOCKET JOINT

CROSS REFERENCE TO RELATED APPLICATION

This is a U.S. Non-Provisional patent application claiming the benefit of French Patent Application Number FR1363296 filed on 20 Dec. 2013 (20 Dec. 2013), which is incorporated herein by reference in its entirety.

TECHNICAL FIELD OF THE INVENTION

The invention relates to a device for measuring the wear of a ball-and-socket joint, a ball-and-socket joint incorporating that device and a method for measuring the wear of such a ball-and-socket joint.

BACKGROUND OF THE INVENTION

The invention in particular relates to the ball-and-socket joints used in the control mechanism of a helicopter.

A helicopter comprises a primary rotor and a tail rotor on which blades are mounted in an articulated manner. By changing the incidence of the blades, the pilot can steer the helicopter in the desired direction.

More specifically, the pilot actuates a control stick that acts on a mechanism for controlling the incidence of the blades. This mechanism comprises an oscillating plate that is mounted on the rotor and that is connected to each of the blades of the rotor by connecting rods and levers. This oscillating plate can pivot around two directions perpendicular to the main axis of the rotor so as to drive the rotation of the levers. A lever is connected to a connecting rod by a ball-and-socket joint, which makes it possible to transmit the rotational movement and modify the incidence of the blades.

A ball-and-socket joint comprises a first ring, for example cylindrical, and a second spherical ring. The first ring comprises a spherical housing in which the second ring is arranged. The first ring is for example secured to a lever, while the second ring is secured to a connecting rod. A lining, or trim, is inserted between the outer ring and the inner ring. It is a solid lubricant with a very low frictional torque. This trim makes it possible to keep the rings of the ball-and-socket joint centered on a same point and limits the friction during the rotation of one ring relative to the other.

However, after a certain number of flight hours, the ball-and-socket joints become worn and a clearance is created between the outer ring and the inner ring. Thus, a relative movement between the outer ring and the inner ring is possible, with the result that the ball-and-socket joint no longer has the desired kinematics. In practice, that clearance within the ball-and-socket joints can make the helicopter uncontrollable. The wear of the ball-and-socket joints depends on the load conditions of the helicopter and on the flight conditions. Thus, the ball-and-socket joints of the oscillating plate do not each have the same wear speed.

It is therefore important to measure the degree of wear of each ball-and-socket joint of the control mechanism for the helicopter regularly. Currently, this measurement is done mechanically, i.e., one ring among the outer ring and the inner ring of the ball-and-socket joint is blocked while the other ring is subjected to a load. By measuring the relative movement between the outer ring and the inner ring, it is possible to deduce the relative clearance thereof between the rings of the ball-and-socket joint, and therefore the wear of the latter. The problem with this method is that it requires the complete disassembly of the oscillating plate.

Furthermore, in light of the number of ball-and-socket joints included in an oscillating plate, the mechanical measurement of the wear of the set of ball-and-socket joints is particularly long, with the result that the helicopter can be immobilized for several hours, or even several days. To resolve these drawbacks, it remains known from US-A-2009/0087253 to incorporate a capacity sensor comprising two electrodes, respectively connected to the two rings of the ball-and-socket joint, into the ball-and-socket joint. The two rings being separated by an electrically insulating lining, they therefore form a capacitor structure with the latter. The variation of the capacity of the capacitor thus formed reflects the wear of the ball-and-socket joint. However, it is difficult to obtain a precise capacity value of the capacitor via a direct measurement.

SUMMARY OF THE INVENTION

The invention more particularly aims to resolve these drawbacks by proposing a method making it possible to measure the wear of a ball-and-socket joint more precisely.

To that end, the invention relates to a device for measuring the wear of a ball-and-socket joint comprising a first ring, which delimits a spherical housing, a second spherical ring, which is positioned concentrically in the housing of the first ring, and a lining, which is made from an elastically insulating material and is inserted between the second ring and the spherical housing of the first ring, this device being adapted to measure the wear of the lining and comprising at least two electrodes provided to be connected to the first ring and the second ring, respectively, or to the lining, so as to form a capacitor structure and means for measuring the capacity of the capacitor thus formed. According to the invention, the device further comprises an electronic circuit, which is a resonant circuit including the capacitor, an inductance and a resistance positioned in series.

Owing to the invention, the variation of the capacity of the capacitor can be evaluated by comparing the quantity of energy dissipated in the resistance when the oscillating circuit is excited at its resonance frequency. In fact, in new condition, the frequency of the excitation signal precisely corresponds to the resonance frequency of the circuit and all of the energy is dissipated in the resistance. However, the capacity of the capacitor varies when the ball-and-socket joint becomes worn and the resonance frequency of the circuit changes, with the result that only part of the energy is dissipated in the resistance. Therefore, the degree of wear of the ball-and-socket joint may be measured by evaluating the quantity of energy that is not dissipated in the resistance of the circuit. It is then possible to situate the status of the ball-and-socket joint in a lifetime model. This model also accounts for the number of flight hours and can predict the number of flight hours remaining for the ball-and-socket joint before the latter deteriorates.

According to advantageous but optional aspects of the invention, a device for measuring the wear of a ball-and-socket joint may incorporate one or more of the following features, considered in any technically allowable combination:

The device further comprises an electronic circuit, which is a resonant circuit including the capacitor, an inductance and a resistance positioned in series.

The electronic circuit is a short-circuited line and the means for measuring the capacity of the capacitor include a reflectometer and an excitation module that are positioned on one side of the line.

The device comprises a radio identification marker, suitable for communicating the measured capacity of the capacitor to a receiver.

The invention also relates to a ball-and-socket joint, comprising a first ring, which delimits a spherical housing, a second spherical ring, which is positioned concentrically in the housing of the first ring, and a lining, which is made from an electrically insulating material and which is interposed between the second ring and the spherical housing of the first ring. According to the invention, the ball-and-socket joint further incorporates a device for measuring the wear of the lining as previously described that is at least partially onboard in a fixed ring of the ball-and-socket joint, chosen between the first ring and the second ring.

The invention lastly relates to a method for measuring the wear of a ball-and-socket joint equipped with or incorporating a measuring device as previously described. This method comprises a step consisting of measuring the capacity of the capacitor formed within the ball-and-socket joint.

According to advantageous, but optional aspects of the invention, the ball-and-socket joint may incorporate one or more of the following features, considered in any technically allowable combination:

The measuring device is incorporated into a housing delimited on an inner radial surface of the first ring.

The measuring device comprises several pairs of electrodes that travel the lining to cover the entire circumference thereof.

Etchings for receiving conductive wires are drawn on an inner radial surface of the first ring and/or on an outer radial surface of the second ring.

The etchings are varnished with an insulating coating to electrically isolate the conductive wires.

Conductive wires are incorporated on an inner radial surface of the first ring and/or on an outer radial surface of the second ring by depositing carbon powder.

The electrodes are formed at the end of the conductive wires that are placed in the filling of the fabric of the lining.

According to advantageous, but optional aspects of the invention, a method for measuring the wear of a ball-and-socket joint may incorporate one or more of the following features, considered in any technically allowable combination:

The capacity of the capacitor is measured by exciting a resonant circuit with an electric pulse, which is a wave whereof the frequency is equal to the resonance frequency of the electronic circuit for a predetermined capacity value, for example equal to the capacity of the ball-and-socket joint in new condition.

The variation of the capacity of the capacitor, in particular due to the wear of the ball-and-socket joint, drives the change in resonance frequency of the electronic circuit and the formation of a reflected wave at the end of the line, which is measured by a reflectometer.

The capacity of the capacitor is deduced from the ratio between the resonance frequency of the circuit for a predetermined capacity value, for example equal to the capacity of the ball-and-socket joint in new condition, and the frequency of the reflected wave.

The value of the measured capacity of the capacitor is transmitted to a receiver by radio.

BRIEF DESCRIPTION OF THE DRAWINGS

The invention and other advantages thereof will appear more clearly in light of the following description of two embodiments of a method for measuring a ball-of-socket joint according to its principle, done in reference to the drawings, in which:

FIG. 1 is a half-sectional perspective view of a ball-and-socket joint incorporating a device for measuring wear according to the invention, FIG. 2 is a diagram illustrating a measuring method according to the invention, which makes it possible to measure the wear of the ball-and-socket joint of FIG. 1, that diagram including a cross-sectional view of the ball-and-socket joint along plane II of FIG. 1, FIG. 3 is a diagram similar to FIG. 2, illustrating a second embodiment of a method for measuring the wear of the ball-and-socket joint of FIG. 1, and FIG. 4 is an enlarged view of circle IV, shown diagrammatically in FIG. 3.

DETAILED DESCRIPTION OF SOME EMBODIMENTS

FIG. 1 shows a ball-and-socket joint 2. This ball-and-socket joint is in particular used in a control mechanism for controlling the movement of a helicopter. The mechanism comprises an oscillating plate, which is mounted on the rotor of the helicopter and which makes it possible, using connecting rods connected to the blades of the rotor, to change the incidence of the blades. These connecting rods are actuated by levers supported by the plate, the transmission of the rotational movement between a lever and a connecting rod being done by the ball-and-socket joint 2.

The ball-and-socket joint 2 comprises a cylindrical outer ring 4 and a spherical inner ring 6. The outer ring 4 delimits a spherical housing O4 for receiving the inner ring 6 and the center of that spherical housing O4 coincides with the center of the inner ring 6. A trim or lining 8 is inserted between the inner ring 6 and the outer ring 4. In general, the lining 8 is fastened to the inner radial surface of the outer ring 4, in particular by gluing. This lining 8 is a solid lubricant, formed by a fabric of Teflon and glass fibers, impregnated with resin. The lining 8 has a very low frictional torque, so as to limit the friction of the rings 4 and 6. It makes it possible to avoid any relative movement between the outer ring 4 and the inner ring 6, i.e., it keeps the inner ring 6 at the center of the spherical housing of the outer ring 4. In practice, the outer ring 4 and the inner ring 6 are each connected to the connecting rod, or a lever not shown in FIG. 1. Thus, the inner ring 6 is provided with an opening O6 for the passage of a connecting rod not shown. In the example, one ring among the inner ring 6 and the outer ring 4 is fixed. Generally, the outer ring 4 is fixed and the inner ring 6 rotates inside the ring 4.

The ball-and-socket joint 2 becomes worn after a certain usage period in a more or less pronounced manner based on the load conditions to which it is subjected. That wear results in a relative movement between the outer ring 4 and the inner ring 6, i.e., the thickness of the lining 8 decreases in certain places. In the case of a helicopter, it is therefore important to measure the degree of wear of each ball-and-socket joint equipping the control mechanism to avoid incidence flaws of the blades. In fact, such flaws can make the helicopter uncontrollable for the pilot.

A method for measuring the wear of the ball-and-socket joint 2 is shown in FIG. 2. As shown in that figure, the ball-and-socket joint 2 is equipped with a device for measuring wear. That device is an external device, i.e., it is removable and can be attached to a standard ball-and-socket joint during the maintenance phase of the helicopter.

That device comprises an electronic system that is mounted on the ball-and-socket joint 2 and comprises an electronic circuit 22. In the electronic circuit 22, the ball-and-socket joint 2 can be modeled as a capacitor C. In fact, the lining 8 is an electrical insulator positioned between two metal frameworks, which, in this example, are formed by the outer ring 4 and the inner ring 6. This is possible because the inner ring 6 and the outer ring 4 are made from an electrically conductive material, in particular metal. In practice, one electrode 42 is connected to the outer ring 4 and another electrode 62 is connected to the inner ring 6. The two electrodes 42 and 62 are shown in FIG. 2 by rectangles positioned at the end of conductive wires. The two electrodes are either connected to outlets positioned on the rings 4 and 6, or fastened directly on the rings 4 and 6, in particular by gluing. The advantage of using the rings 4 and 6 as frameworks of the capacitor C is that the overall capacity variation of the lining 8 is obtained. The lining 8 being insulating, there is no passage of current between the outer ring 4 and the inner ring 6, but the capacitor C is passed through by an electric field, some current lines 100 of which are shown in FIG. 2, between the two electrodes 42 and 62 for connecting the rings 4 and 6 of the ball-and-socket joint 2.

The circuit 22 also comprises an impedance or coil L and a resistance R. The electronic circuit 22 in which the ball-and-socket joint 2 is placed is therefore a serial RLC circuit that is a resonant circuit. Furthermore, the circuit 22 is a short-circuited line, i.e., one end of the line is connected to a source, here a reflectometer 14, while the other end T is a short circuit, i.e., the terminus T has a zero impedance. The reflectometer 14 is coupled to an excitation module 16 that is used to deliver an electric pulse, or alternating excitation voltage Ei, to the circuit 22. This variable excitation voltage Ei is in particular sinusoidal and is transmitted by a waveguide 12 to the circuit 22. In practice, the waveguide 12 is a coaxial cable. The reflectometer 14 is a measuring instrument, in particular used in telecommunications or electricity distribution grids to detect faults in electrical cables.

For a new ball-and-socket joint, the capacity of the capacitor C formed by the inner ring 6, the outer ring 4 and the insulator 8 is known, since it depends on the thickness of the lining 8. Consequently, the resonance frequency of the circuit 22 is also known. When the electronic circuit is subjected to a voltage whereof the frequency is equal to the resonance frequency, all of the energy is dissipated in the resistance R, i.e., the circuit is adapted in impedance. Thus, the reflectometer does not perceive energy reflected by the circuit 22.

However, when the ball-and-socket joint becomes worn, the thickness of the lining 8 decreases and the capacity of the capacitor C varies. Consequently, the resonance frequency of the circuit also changes. Thus, when the electronic circuit 22 is stressed with a pulse whose frequency is equal to the resonance frequency calculated for a new ball-and-socket joint, all of the energy is not dissipated in the resistance R, i.e., part Er of the energy is reflected at the end of the line. That energy or electric wave Er returns via the waveguide 12 to the reflectometer 14, which is capable of reconstituting the received signal. In FIG. 2, the energy or electric wave Er is shown in broken lines, since it only exists when the circuit 22 is not adapted in impedance, i.e., when the resonance frequency of the circuit differs from the resonance frequency of the ball-and-socket joint in new condition.

Thus, the reflectometer 14 can measure the frequency of the reflected wave. However, the ratio between the resonance frequency for a new ball-and-socket joint and the frequency of the reflected wave Er is directly proportional to the capacity of the capacitor C. Consequently, the reflectometer 14 can deduce the capacity of the capacitor. Wisely, positioning the capacitor C, the coil L and the resistance R on a short circuit by makes it possible to test that line with a reflectometer, since the wave can reflect at the end of the line if it is not completely dissipated.

The capacity value is communicated by radio waves to a receiver 20, as shown by the wave transmission symbol in FIG. 2. To that end, the ball-and-socket joint 2 includes a radio identification marker 18. This radio identification marker 18 is a radio tag, which is incorporated into the ball-and-socket joint 2 and comprises an antenna (not shown). The receiver 20 is therefore a reader, i.e., a receiver base. Furthermore, the receiver 20 further transmits radio frequencies to activate the radio identification marker 18. In fact, the receiver 20 provides energy to the marker 18 so that the latter can operate. In that case, the receiver 20 operates as a transmitter base while the radio identification marker 18 works as a receiver base. More specifically, the energy provided to the marker 18 is used to generate the excitation pulse Ei of the circuit 22. Thus, the receiver 20 and the marker 18 communicate with each other, as shown by the two-way arrow in FIG. 2.

To recover the capacity value of a ball-and-socket joint, the receiver 20 should be brought closer to the ball-and-socket joint to be at the right distance. In practice, that distance is comprised between 2 m and 8 m. Furthermore, the marker 18 communicates the reference of the ball-and-socket joint associated with the capacitive measurement.

The variation of the capacity of the capacitor between the measured value and the known value of the ball-and-socket joint and the new condition makes it possible to deduce the thickness variation of the lining 8, and therefore the degree of wear of the ball-and-socket joint. In practice, the thickness of the lining 8 can vary from a thickness of 200 μm to a thickness of 50 μm. The resulting capacity variation is approximately ten picofarads, which is difficult to measure without using a specific technique, such as reflectometry.

By recovering the maintenance data for each ball-and-socket joint, it is possible to inventory the data for each ball-and-socket joint in a database with a reference number, a degree of wear and the number of hours of flight. In this way, it is possible to develop a lifetime model for each ball-and-socket joint, i.e., a model making it possible to predict approximately how many hours each ball-and-socket joint can hold before beginning to deteriorate.

In an alternative that is not shown, similar to the first embodiment, the device for measuring the wear of the ball-and-socket joint 2 is incorporated into the ball-and-socket joint. That device is onboard, in whole or in part, on the ball-and-socket joint, for example with a fixed ring of the ball-and-socket joint. In particular, the device can be incorporated into a housing arranged on the inner radial surface of the outer ring 4. Two electrodes come from the device and are respectively connected to the rings 4 and 6. The method for measuring the capacity of the capacitor is identical to the embodiment described above.

FIGS. 3 and 4 show a second embodiment of a method for measuring the wear of the ball-and-socket joint 2. In the rest of the description, the component elements of the ball-and-socket joint or the device for measuring the wear of the ball-and-socket joint that are identical or that perform the same function bear the same references, while the additional elements or elements that work differently from the first embodiment bear other numerical references.

In this second embodiment, the frameworks of the capacitor are not respectively formed by the inner and outer rings, but by two electrodes 82 and 84, which are housed in the lining 8, and between which a difference in potential is applied.

More specifically, as shown in FIG. 4, the electrodes 82 and 84 are formed at the end of conductive wires placed in the filling of the fabric of the lining 8. In FIG. 4, only the parts of the fabric in the vicinity of the electrodes 82 and 84 are shown, the rest of the lining being formed similarly. The conductive wires supporting the electrodes 82 and 84 come from a measuring device received in a housing 46 delimited on the inner radial surface of the outer ring 4. The device for measuring the capacity of the capacitor is therefore on the ball-and-socket joint, in particular the fixed ring, here considered to be the outer ring 4. The wires extend toward components of a circuit 22 identical to that of FIG. 2, as shown by the dotted lines in FIG. 4.

Current lines 100 are then generated between the two electrodes 82 and 84, and the material space between the two electrodes forms the insulator of a capacitor C having the two electrodes as conductive frameworks. The measurement of the capacity of that capacitor C reflects the localized wear of the lining 8 in the location where the electrodes are placed. In practice, several pairs of electrodes (not shown) travel the lining 8 to cover the entire circumference of the lining, which makes it possible to have an overall picture of the wear of the lining 8. This is referred to as a meshing of the ball-and-socket joint. The number of pairs of electrodes used varies in particular based on the difference in potential applied to the electrodes, the distance at which they are placed from one another and the insulating capacity of the lining 8. The capacity of the capacitor structure C is measured using a device similar or identical to that of FIG. 2, except that it is incorporated into the fixed ring of the ball-and-socket joint.

In an alternative that is not shown, etchings for receiving conductive wires are drawn on the outer radial surface of the inner ring 6 and/or on the inner radial surface of the outer ring 4. These etchings may be of the skinny filling type, i.e., fine etchings designed for the passage of conductive wires, as done in printed circuits. The etchings are varnished with an insulating coating so as to insulate the conductive wires. These conductive wires bear electrodes that are submerged in the lining 8. An electric field is created between two electrodes, which generates current lines, and it is possible to measure the capacity of the capacitor formed by the two electrodes and the material portion separating the two electrodes.

According to another alternative design, conductive wires are incorporated on the inner radial surface of the ring 4 and/or on the outer radial surface of the ring 6. These wires are incorporated into one or each ring by depositing carbon powder. This carbon deposition may be done using any suitable technique. In particular, one technique consists of using a specific mask. That mask hides certain portions of the ring during the surface treatment of the ring and leaves certain zones free to be treated. A passivation layer is first applied on the free zones, so as to electrically insulate the free zones of the ring. These free zones are in fact passage lines for conductive wires, to incorporate electrodes into the lining. Once insulated, the free zones of the mask are subjected to a carbon deposition, which is in particular done in a tight gas enclosure. Conductive wires are thus obtained that are directly incorporated into the ring, which are electrically insulated from the latter. As before, the conductive wires bear electrodes, which are submerged in the lining and on which a potential difference is applied. These electrodes form a capacitor with the lining, the capacity variation of which reflects the wear. The capacity measurement can be done by the same type of device as in the embodiment of FIG. 2.

In one alternative that is not shown, means other than reflectometry can be used to measure the capacity of the capacitor. For example, it is possible to use a bridge mounting coupled with an amplification circuit, a microcontroller or an operational amplifier mounted alone.

In one alternative that is not shown, it is possible to use several pairs of frameworks within the ball-and-socket joint, the frameworks of each framework pair being separated by the lining and measuring the capacity variation in a particular zone. The set of measurements is next averaged to obtain a global picture of the wear of the ball-and-socket joint.

In one alternative that is not shown, the ball-and-socket joint 2 further incorporates means for reducing noise at the capacity value of the capacitor. These noise reducing means are for example a filter, used to smooth the capacity variation curve. They can also include a temperature gauge, which is sensitive to sudden variations in the capacity of the capacitor, and therefore the noise.

The features of the embodiments and alternatives considered above can be combined to provide new embodiments of the invention.

The invention claimed is:

1. A device for measuring the wear of a ball-and-socket joint comprising:
    a first ring, which delimits a spherical housing;
    a second spherical ring, which is positioned concentrically in the housing of the first ring;
    a lining, which is made from an electrically insulating material and, which is interposed between the second ring and the spherical housing of the first ring,
    wherein the device is placed in a filling of a fabric of the lining and adapted to measure the wear of the lining by including:
        at least two electrodes comprising a first electrode connected to a first connection point of the lining and a second electrode connected to a second connection point of the lining to form a capacitor structure, and
        a capacitance measuring feature for measuring a capacitance of the capacitor structure thus formed;
    an electronic circuit, which is a resonant circuit including the capacitor structure, an inductance and a resistance positioned in series; and
    a radio identification marker incorporated into the ball-and-socket joint, the radio identification marker communicating and transmitting a value of the capacitance of the capacitor structure and a reference number of the ball-and-socket joint to a receiver, the radio identification marker being a radio tag comprising an antenna.

2. The device according to claim 1, wherein:
    the electronic circuit is a short-circuited line, and
    the capacitance measuring feature for measuring the capacitance of the capacitor structure includes a reflectometer and an excitation module that are positioned on one side of the line.

3. A ball-and-socket joint, comprising:
a first ring, which delimits a spherical housing;
a second spherical ring, which is positioned concentrically in the spherical housing of the first ring,
a lining, which is made from an electrically insulating material and which is interposed between the second ring and the spherical housing of the first ring,
a device for measuring wear, wherein the device is placed in a filling of a fabric of the lining and adapted to measure the wear of the lining by including:
  at least two electrodes comprising a first electrode connected to a first connection point of the lining and a second electrode connected to a second connection point of the lining to form a capacitor structure,
  a capacitance measuring feature for measuring a capacitance of the capacitor structure thus formed;
an electronic circuit, which is a resonant circuit including the capacitor structure, an inductance and a resistance positioned in series; and
a radio identification marker incorporated into the ball-and-socket joint, the radio identification marker communicating and transmitting a value of the capacitance of the capacitor structure and a reference number of the ball-and-socket joint to a receiver, the radio identification marker being a radio tag comprising an antenna.

4. The ball-and-socket joint according to claim 3, wherein the measuring device is incorporated into a housing delimited on an inner radial surface of the first ring.

5. A method for measuring the wear of a ball-and-socket joint, the method comprising:
accessing a ball-and-socket joint comprising:
  a first ring, which delimits a spherical housing,
  a second spherical ring, which is positioned concentrically in the housing of the first ring,
  a lining, which is made from an electrically insulating material and, which is interposed between the second ring and the spherical housing of the first ring,
  a measuring device placed in a filling of a fabric of the lining,
measuring by the measuring device the wear of the lining by forming a capacitor structure from at least two electrodes comprising a first electrode connected to a first connection point of the lining and a second electrode connected to a second connection point of the lining;
measuring a capacitance of the capacitor structure thus formed by a capacitance measuring feature; and
communicating and transmitting by a radio identification marker a value of the capacitance of the capacitor structure and a reference number of the ball-and-socket joint to a receiver; the radio identification marker being incorporated into the ball-and-socket joint, the radio identification marker being a radio tag comprising an antenna.

6. The method according to claim 5, wherein step of measuring the capacitance of the capacitor structure is accomplished by exciting a resonant circuit with an electric pulse, which is a wave whereof the frequency is equal to the resonance frequency of the electronic circuit for a predetermined capacitance value.

7. The method according to claim 6, wherein the predetermined capacitance value is equal to the capacitance of the capacitor structure in new condition.

8. The method according to claim 6, wherein variation of the capacitance of the capacitor structure, due to wear of the ball-and-socket joint, causes a change in resonance frequency of the electronic circuit and the formation of a reflected wave at the end of the line, which is measured by a reflectometer.

9. The method according to claim 8, wherein the capacitance of the capacitor structure is deduced from a ratio between the resonance frequency of the circuit for a predetermined capacitance value, and the frequency of the reflected wave.

* * * * *